US012780767B2

(12) United States Patent
Tsuna et al.

(10) Patent No.: US 12,780,767 B2
(45) Date of Patent: Nov. 3, 2026

(54) METHOD FOR PRODUCING HALOGENOBICYCLO[1.1.1]PENTANE

(71) Applicant: FUJIFILM Corporation, Tokyo (JP)

(72) Inventors: Kazuhiro Tsuna, Kanagawa (JP); Koichi Iwasaki, Kanagawa (JP); Kenji Wada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 376 days.

(21) Appl. No.: 18/434,872

(22) Filed: Feb. 7, 2024

(65) Prior Publication Data

US 2024/0279143 A1 Aug. 22, 2024

Related U.S. Application Data

(63) Continuation of application No. PCT/JP2022/032636, filed on Aug. 30, 2022.

(30) Foreign Application Priority Data

Sep. 13, 2021 (JP) ................................ 2021-148840

(51) Int. Cl.
*C07C 17/10* (2006.01)
*C07C 23/20* (2006.01)

(52) U.S. Cl.
CPC .............. *C07C 17/10* (2013.01); *C07C 23/20* (2013.01); *C07C 2602/38* (2017.05)

(58) Field of Classification Search
CPC ..... C07C 17/10; C07C 23/20; C07C 2602/38; C07C 13/547
See application file for complete search history.

(56) References Cited

U.S. PATENT DOCUMENTS

| | | | |
|---|---|---|---|
| 10,513,483 | B2 | 12/2019 | Suzuki et al. |
| 11,339,103 | B2 | 5/2022 | Pinchman et al. |
| 11,858,873 | B2 | 1/2024 | Hong et al. |
| 2017/0081295 | A1 | 3/2017 | Bunker |

FOREIGN PATENT DOCUMENTS

| | | |
|---|---|---|
| CN | 109071409 | 12/2018 |
| CN | 110117215 | 8/2019 |
| CN | 111164063 | 5/2020 |
| WO | 2017205459 | 11/2017 |
| WO | 2020252661 | 12/2020 |

OTHER PUBLICATIONS

Alber, F. et al., Solvent-free [1.1.1]propellan form 1,3-diiodobicyclo[1.1.1]pentane, Kurzmitelung/Short Communication, Chemische Berichte, vol. 125, issue 3, pp. 757-758 (Year: 1992).*
Belzner, J. et al., Concrning the Synthesis of [1.1.1]propellane, Chemische Berichte, vol. 122, issue 2,pp. 387-398 (Year: 1989).*
Kireev, S.V., et al., Study of molecular iodine, iodate ions, iodide ions, and triiodide ions solutions absorption in the UV and visible light spectral bands, Laser Phys, 25, 11 pages (Year: 2015).*
Wiberg, K. B., et al., Reacton s of [1.1.1]propellane, J. Am. Chem. Soc., vol. 112, No. 6, pp. 2194-2216 (Year: 1990).*
Zefirov, N.S., et al., Reactions of [1.1.1]propellane, Journal of Organic Chemistry USSR, vol. 26, No., 11, pp. 2002-2014 (Year: 1990).*
Kenneth B. Wiberg et al., “Propellane: Reaction with free radicals”, Tetrahedron Letters, Jan. 1986, pp. 1553-1556.
Semnani, Abolfazl et al., “Spectrophotometric Study of the Complexation of Iodine and Bromine with Tetrabutylammonium Halides and Cryptand 222 in Dichloromethane Solution”, Mar. 2004, pp. 1-6.
Mitsumi Takeda et al., “Direct lactonization from 1,3-dienes and malonate esters mediated by a combination of iodine and visible light”, Tetrahedron Letters, Nov. 2019, pp. 1-3.
Kian Donnelly et al., “A continuous flow synthesis of [1.1.1]propellane and bicyclo[1.1.1]pentane derivatives”, Chem. Comm., Feb. 2021, pp. 1-5.
“International Search Report (Form PCT/ISA/210) of PCT/JP2022/032636,” mailed on Nov. 22, 2022, with English translation thereof, pp. 1-6.
“Written Opinion of the International Searching Authority (Form PCT/ISA/237) of PCT/JP2022/032636,” mailed on Nov. 22, 2022, with English translation thereof, pp. 1-8.
Semnani, Abolfazl et al., “Spectrophotometric Study of the Complexation of Iodine and Bromine with Tetrabutylammonium Halides and Cryptand 222 in Dichloromethane Solution”, Iranian Journal of Chemistry and Chemical Engineering, Mar. 2004, pp. 1-6.
“Search Report of Europe Counterpart Application”, issued on Feb. 17, 2025, pp. 1-6.
“Office Action of Japan Counterpart Application”, issued on Feb. 4, 2025, with English translation thereof, pp. 1-6.
N. S. Zefirov et al., “Reactions of [1.1.1]Propellane”, Journal of Organic Chemistry USSR, Nov. 1990, pp. 2002-2014.
“First Office Action Notification of China Counterpart Application”, with English translation thereof, issued on Aug. 14, 2026, pp. 1-16.

* cited by examiner

*Primary Examiner* — Yate’ K Cutliff
(74) *Attorney, Agent, or Firm* — JCIPRNET

(57) ABSTRACT

Provided is a method for producing halogenobicyclo[1.1.1]pentane, including a step (a) of reacting 1,1-dibromo-2,2-bis(chloromethyl)cyclopropane with an organometallic reagent in a solvent including acyclic ether having 5 or more carbon atoms to obtain [1.1.1]propellane, and
a step (b) of reacting the obtained [1.1.1]propellane with halogen in a state in which light having a wavelength of 400 nm or less is shielded to obtain halogenobicyclo[1.1.1]pentane.

11 Claims, No Drawings

METHOD FOR PRODUCING HALOGENOBICYCLO[1.1.1]PENTANE

CROSS-REFERENCE TO RELATED APPLICATIONS

This application is a Continuation of PCT International Application No. PCT/JP2022/032636 filed on Aug. 30, 2022, which claims priority under 35 U.S.C. § 119 (a) to Japanese Patent Application No. 2021-148840 filed in Japan on Sep. 13, 2021. Each of the above applications is hereby expressly incorporated by reference, in its entirety, into the present application.

BACKGROUND OF THE INVENTION

1. Field of the Invention

The present invention relates to a method for producing halogenobicyclo[1.1.1]pentane.

2. Description of the Related Art

A bicyclo[1.1.1]pentane (BCP) compound has attracted attention as a biologically active compound. A BCP motif has high three-dimensionality and high biological safety while having biological functionality equivalent to a para-substituted phenyl group, an alkynyl group, a tert-butyl group, and the like, so that it is expected to be applied to drug delivery. In addition, a halide of BCP (halogeno BCP) is a compound useful as a building block, and among these, 1,3-diiodo BCP is actually introduced in synthesis of a pharmaceutical drug candidate compound.

A number of methods of synthesizing the 1,3-diiodo BCP have been proposed. For example, Chem. Commun., 2021, vol. 57, p. 2871 to 2874 discloses that [1.1.1]propellane is obtained by reacting 1,1-dibromo-2,2-bis(chloromethyl)cyclopropane with methyllithium in a diethyl ether solvent, and this [1.1.1]propellane is reacted with iodine to obtain the 1,3-diiodo BCP.

SUMMARY OF THE INVENTION

In the synthesis of the [1.1.1]propellane which is an intermediate of the synthesis of halogeno BCP useful as a building block, it has been known that the 1,1-dibromo-2,2-bis(chloromethyl)cyclopropane is reacted with methyllithium in the diethyl ether solvent. However, there are restrictions on the application to industrial production, such as the fact that the diethyl ether is a special inflammable material.

In addition, as a result of studies by the present inventors, in a case where [1.1.1]propellane is obtained using the 1,1-dibromo-2,2-bis(chloromethyl)cyclopropane as a starting material and the [1.1.1]propellane is halogenated to obtain halogeno BCP, yield of the obtained halogeno BCP is low, and it is presumed that there are some restrictions on improving the yield.

An object of the present invention is to provide a novel method for producing halogeno BCP, which is suitable for industrial production and can effectively increase yield.

The object of the present invention has been achieved by the following methods.

[1]

A method for producing halogenobicyclo[1.1.1]pentane, comprising:

- a step (a) of reacting 1,1-dibromo-2,2-bis(chloromethyl) cyclopropane with an organometallic reagent in a solvent including an acyclic ether solvent having 5 or more carbon atoms to obtain [1.1.1]propellane; and
- a step (b) of reacting the obtained [1.1.1]propellane with halogen in a solvent including an acyclic ether solvent having 5 or more carbon atoms in a state in which light having a wavelength of 400 nm or less is shielded to obtain halogenobicyclo[1.1.1]pentane.

[2]

The method for producing halogenobicyclo[1.1.1]pentane according to [1], in which the organometallic reagent includes at least one of alkyllithium or aryllithium.

[3]

The method for producing halogenobicyclo[1.1.1]pentane according to [2], in which the alkyllithium has 2 to 10 carbon atoms.

[4]

The method for producing halogenobicyclo[1.1.1]pentane according to [2] or [3], in which the aryllithium is phenyllithium.

[5]

The method for producing halogenobicyclo[1.1.1]pentane according to any one of [2] to [4], in which the alkyllithium is butyllithium.

[6]

The method for producing halogenobicyclo[1.1.1]pentane according to any one of [1] to [5], in which a reaction temperature of the step (a) is set to 0° C. or lower.

[7]

The method for producing halogenobicyclo[1.1.1]pentane according to any one of [1] to [6], in which, in the step (a) and the step (b), the acyclic ether solvent has 5 to 10 carbon atoms.

[8]

The method for producing halogenobicyclo[1.1.1]pentane according to [7], in which, in the step (a) and the step (b), the acyclic ether solvent has 5 or 6 carbon atoms.

[9]

The method for producing halogenobicyclo[1.1.1]pentane according to any one of [1] to [8], in which the halogen is iodine.

[10]

The method for producing halogenobicyclo[1.1.1]pentane according to any one of [1] to [9], in which the halogenobicyclo[1.1.1]pentane is diiodobicyclo[1.1.1]pentane.

[11]

The method for producing halogenobicyclo[1.1.1]pentane according to any one of [1] to [10], in which a step of distilling the [1.1.1]propellane is not provided.

In the present invention or the specification, any numerical range expressed using "to" refers to a range including the numerical values before and after the "to" as a lower limit value and an upper limit value, respectively.

The method for producing halogeno BCP according to the aspect of the present invention is suitable for industrial production and can effectively increase yield of the obtained halogeno BCP.

DESCRIPTION OF THE PREFERRED EMBODIMENTS

The method for producing halogeno BCP according to the embodiment of the present invention (hereinafter, also referred to as a production method according to the embodiment of the invention) includes a step (a) of present reacting 1,1-dibromo-2,2-bis(chloromethyl)cyclopropane with an organometallic reagent in a solvent including acyclic ether having 5 or more carbon atoms to obtain [1.1.1]propellane, and a step (b) of reacting the obtained [1.1.1]propellane with halogen in a solvent including an acyclic ether solvent having 5 or more carbon atoms in a state in which light having a wavelength of 400 nm or less is shielded to obtain halogeno BCP.

[Step (a)]

<Acyclic Ether Solvent Having 5 or More Carbon Atoms>

The number of carbon atoms in the acyclic ether solvent having 5 or more carbon atoms, which is used in the production method according to the embodiment of the present invention, is preferably 5 to 10, more preferably 5 to 8, still more preferably 5 to 7, and even more preferably 5 or 6.

Conventionally, in the step of reacting 1,1-dibromo-2,2-bis(chloromethyl)cyclopropane with an organometallic reagent to obtain [1.1.1]propellane, diethyl ether has been widely used to dissolve the organometallic reagent such as methyllithium. However, the diethyl ether is a special inflammable material, and there are certain restrictions on the use thereof in industrial production. In the present invention, an acyclic ether solvent having 5 or more carbon atoms is used instead of the diethyl ether. Even in a case where such a solvent is used, a sufficiently high reaction efficiency can be achieved as in the case where the diethyl ether is used. In a case where a cyclic ether, an aromatic compound, or the like is used as the solvent, yield of the obtained [1.1.1]propellane is deteriorated. That is, in the balance between a target reaction and a side reaction, it is considered that the solvent effect of the acyclic ether having 5 or more carbon atoms effectively acts to proceed with the target reaction.

It is more preferable that the acyclic ether solvent having 5 or more carbon atoms is at least one of cyclopentylmethyl ether or methyl tert-butyl ether.

The solvent used in the step (a) may include a solvent other than the acyclic ether solvent having 5 or more carbon atoms (that is, a mixed solvent may be used). The solvent other than the acyclic ether solvent having 5 or more carbon atoms is not particularly limited, and can be appropriately used as long as the effects of the present invention are not impaired. Preferred examples of the solvent other than the acyclic ether solvent having 5 or more carbon atoms include aliphatic hydrocarbon solvents (for example, hexane, cyclohexane, pentane, heptane, and the like). In a case where the solvent used in the step (a) is a mixed solvent including the acyclic ether solvent having 5 or more carbon atoms and other solvents, as an amount ratio thereof, in terms of mass ratio, [Acyclic ether solvent having 5 or more carbon atoms]/[Solvent other than acyclic ether solvent having 5 or more carbon atoms] is preferably 1/10 or more, more preferably 1/5 or more, still more preferably 1/2 or more, and even more preferably 1/1 or more. That is, a proportion of the acyclic ether solvent having 5 or more carbon atoms in the solvent is preferably 50% by mass or more, 60% by mass or more, or 65% by mass or more.

<Organometallic Reagent>

The organometallic reagent used in the present invention is not particularly limited as long as it is a reagent which reacts with 1,1-dibromo-2,2-bis(chloromethyl)cyclopropane to generate [1.1.1]propellane. For example, alkyllithium, aryllithium, or the like can be widely used.

An alkyl group of the alkyllithium may be linear or branched, and is preferably linear. The number of carbon atoms in the alkyllithium is preferably 2 to 10, more preferably 3 to 8, still more preferably 3 to 6, and even more preferably 3 to 5. The alkyllithium is preferably butyllithium, and particularly preferably n-butyllithium. In a case where methyllithium is used, bromomethane which is designated as an ozone layer depleting substance is by-produced. From this viewpoint, the number of carbon atoms in the alkyllithium is preferably 2 or more.

The number or carbon atoms in an aryl group of the aryllithium is preferably 6 to 30, more preferably 6 to 20, still more preferably 6 to 15, even more preferably 6 to 12, and even still more preferably 6 to 10. The aryllithium is preferably at least one of phenyllithium, toluyllithium, methoxyphenyllithium, chlorophenyllithium, or naphthyllithium, and among these, phenyllithium is preferable.

In addition, it is also preferable to use the above-described alkyllithium as the organometallic reagent, together with bromobenzene. In this case, phenyllithium is generated in the reaction system. Such an aspect has an advantage that the phenyllithium can be used in the reaction without reducing activity of the phenyllithium.

<Reaction Conditions of Step (a)>

The step (a) may be a batch-type reaction or a flow-type reaction.

In a case of the batch-type reaction, for example, a solvent including the acyclic ether solvent having 5 or more carbon atoms, and 1,1-dibromo-2,2-bis(chloromethyl)cyclopropane are charged into a container, and preferably in an atmosphere of inert gas (nitrogen gas, rare gas, or the like), a temperature can be controlled to, for example, −100° C. to 20° C. From the viewpoint of improving the yield, the temperature is set to preferably 10° C. or lower, more preferably 0° C. or lower, still more preferably −10° C. or lower, even more preferably -20° C. or lower, even still more preferably −30° C. or lower, further more preferably −40° C. or lower, and even further more preferably −45° C. or lower. In a case where the above-described temperature is shown as a preferred range by specifying the upper and lower limit values, it is preferably −100° C. to 10° C., more preferably −100° C. to 0° C., still more preferably −100° C. to −10° ° C., even more preferably −100° C. to −20° C., even still more preferably −100° C. to −30° C., further more preferably −100° C. to −40° C., and even further more preferably −100° C. to −45° C. The solution and a solution obtained by dissolving the organometallic reagent are mixed with each other at the above-described temperature for reaction. The reaction time is not particularly limited as long as the target reaction can be sufficiently carried out. For example, the reaction time can be set to 30 seconds or more, preferably 1 minute or more, 5 minutes or more, or 10 minutes or more. This reaction time is usually set to 3 hours or less, may be 2 hours or less or 1 hour or less, and is preferably set to 30 minutes or less. In a case where the above-described reaction time is shown as a preferred range by specifying the upper and lower limit values, it is preferably 30 seconds or more and 3 hours or less, 1 minute or more and 2 hours or less, 5 minutes or more and 1 hour or less, or 10 minutes or more and 30 minutes or less. During the reaction, the temperature may be raised or lowered within the above-described temperature range. In addition, from the viewpoint of more reliably suppressing residue of the raw materials, for example, a sufficient reaction may be carried out by initially controlling the temperature at −100° C. to 30° C., and then the temperature may be further raised to −10° C. to 0° C. and retained for a certain period of time. The above-described reaction conditions can be appropriately set while confirming the yield of BCP to be obtained.

In a case of the flow-type reaction, for example, a solution of 1,1-dibromo-2,2-bis(chloromethyl)cyclopropane and a solution of the organometallic reagent are allowed to flow through different flow channels, and both solutions can be combined and reacted while being allowed to flow downstream. Same as described above, the liquid temperature can be controlled to, for example, a temperature of −100° C. to 20° C. In addition, the reaction time can be controlled by the flow time of the combined solution. Same as described above, the reaction time can be set to, for example, 5 minutes or more. As a form of such a flow-type reaction, for example, Chem. Commun., 2021, vol. 57, p. 2871 to 2874 can be referred to.

As the reaction conditions of the step (a), the preferred reaction temperature, reaction time, and the like described in the above batch-type reaction can be applied regardless of the reaction method of the batch-type reaction, the flow-type reaction, and the like.

In the above-described reaction, regardless of the reaction method of the batch-type reaction, the flow-type reaction, and the like, as a reaction molar ratio of 1,1-dibromo-2,2-bis(chloromethyl)cyclopropane and the organometallic reagent, [1,1-dibromo-2,2-bis(chloromethyl)cyclopropane]/[Organometallic reagent] is preferably 1/1.5 to 1/3, more preferably 1/1.9 to 1/2.3, and still more preferably 1/2 to 1/2.2. In addition, a concentration of each of the solution of 1,1-dibromo-2,2-bis(chloromethyl)cyclopropane and the solution of the organometallic reagent is appropriately set according to the purpose. For example, the concentration of the solution of 1,1-dibromo-2,2-bis(chloromethyl)cyclopropane can be set to 0.1% to 30% by mass, preferably 1% to 20% by mass. In addition, the concentration of the solution of the organometallic reagent can be set to 0.1% to 40% by mass, preferably 10% to 30% by mass.

In the step (a), the [1.1.1]propellane may be distilled after the reaction, but the [1.1.1]propellane may be used as it is as a reaction raw material of the next step (b) without being distilled. From the viewpoint of work efficiency, it is preferable that the step (a) does not include a step of distilling the [1.1.1]propellane.

[Step (b)]

In the step (b), the [1.1.1]propellane obtained in the step (a) is reacted with halogen in a solvent including an acyclic ether solvent having 5 or more carbon atoms in a state in which light having a wavelength of 400 nm or less is shielded to obtain halogeno BCP. The halogeno BCP is preferably dihalogeno BCP, and more preferably 1,3-dihalogeno BCP. Examples of the halogen include fluorine, chlorine, bromine, and iodine, and iodine is preferable. That is, the halogeno BCP is more preferably diiodo BCP, and still more preferably 1,3-diiodo BCP.

The acyclic ether solvent having 5 or more carbon atoms, which is used in the step (b), is the same as the acyclic ether solvent having 5 or more carbon atoms, which is described in the step (a), and preferred aspects thereof are also the same. In addition, in a case where the solvent used in the step (b) includes a solvent other than the acyclic ether solvent having 5 or more carbon atoms, an aspect of a mixed solvent is also the same as the aspect described in the step (a), and preferred aspects thereof are also the same. Solvent composition used in the step (a) may be the same as or different from solvent composition used in the step (b). The step (b) may be a batch-type reaction or a flow-type reaction.

In a case of the batch-type reaction, for example, a solution obtained by dissolving the halogen is dropwise added to a solution obtained by dissolving the [1.1.1]propellane obtained in the step (a) in a solvent for mixing, whereby a halide of BCP can be obtained. The reaction can be carried out, for example, by controlling the temperature to −100° C. to 20° C. The reaction temperature is preferably 10° C. or lower and more preferably 5° C. or lower. In addition, the reaction temperature is preferably −50° C. or higher, −30° C. or higher, −20° C. or higher, or −10° C. or higher. In a case where the above-described reaction temperature is shown as a preferred range by specifying the upper and lower limit values, it is preferably −50° C. to 10° C., more preferably −30° C. to 5° C., still more preferably -20° C. to 5° C., and even more preferably −10° C. to 5° C. In addition, the reaction time (including the dropwise addition time) is preferably 0.001 to 600 minutes, more preferably 0.01 to 300 minutes, and still more preferably 0.1 to 60 minutes.

In addition, in the flow-type reaction, a solution of the [1.1.1]propellane obtained in the step (a) and a solution containing the halogen are allowed to flow through different flow channels, and both solutions can be combined and reacted while being allowed to flow downstream. As the reaction temperature, reaction time, and the like, the aspects described in the above batch-type reaction can be applied. As a form of the flow-type reaction, for example, Chem. Commun., 2021, vol. 57, p. 2871 to 2874 can be referred to.

In the above-described reaction, regardless of the reaction method of the batch-type reaction, the flow-type reaction, and the like, as a reaction molar ratio of the [1.1.1]propellane and the halogen, [[1.1.1]propellane]/[Halogen] is preferably 1/0.5 to 1/5, more preferably 1/0.9 to 1/2, and still more preferably 1/1 to 1/1.5.

A concentration of each of the solution of [1.1.1]propellane and the solution of the halogen is appropriately set according to the purpose. For example, the concentration of the solution of [1.1.1]propellane can be set to 0.01% to 50% by mass, preferably 0.1% to 10% by mass. In addition, the concentration of the solution of the halogen can be set to 0.1% to 80% by mass, preferably 10% to 30% by mass.

The reaction of the step (b) is carried out in a state in which light having a wavelength of 400 nm or less is shielded. As a result, the yield of halogeno BCP to be obtained can be significantly increased. The reason for this is not clear, but it is considered that the halogeno BCP is weak to light of a specific wavelength, and decomposition of the generated halogeno BCP can be effectively reduced by shielding the light having a wavelength of 400 nm or less.

A method of shielding the light is not particularly limited, and examples thereof include a method of using a yellow LED as a light source for illumination, a method of using a light source for illumination provided with a cut filter, and a method of using a reactor provided with a reflective material. It is not necessary to shield light having a wavelength longer than 400 nm as long as the light having a wavelength of 400 nm or less is shielded light. In addition, in addition to the shielding of the light having a wavelength of 400 nm or less, a part or all of light having a wavelength longer than 400 nm may be shielded. In addition, it is preferable that the light having a wavelength of 400 nm or less is completely shielded.

The yield in the step (b) (yield in the reaction of halogenating [1.1.1]propellane to obtain halogeno BCP; that is, [Molar amount of generated halogeno BCP]/[Molar amount of [1.1.1]propellane as starting raw material]) is preferably 65% or more, more preferably 70% or more, still more preferably 80% or more, even more preferably 85% or more, even still more preferably 90% or more, and further more preferably 92% or more. Such a high yield can be achieved by shielding the light having a wavelength of 400 nm or less.

The halogeno BCP produced in the step (b) can also be separated and purified. As this separation or purification method, a general method can be appropriately applied. For example, column chromatography, recrystallization, reprecipitation, sublimation, or the like can be applied alone or in combination.

Hereinafter, the present invention will be more specifically described based on Examples, but the present invention is not limited to Examples.

EXAMPLES

Example 1

1,3-diiodo BCP was obtained according to the following scheme.

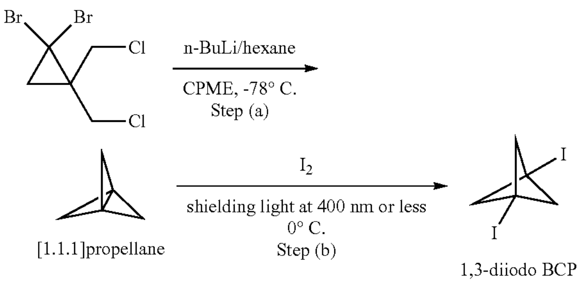

[1.1.1]propellane 1,3-diiodo BCP

[Step (a)]

100 mL of cyclopentyl methyl ether (CPME) and 10 g of 1,1-dibromo-2,2-bis(chloromethyl)cyclopropane were charged into a 500 mL three-neck flask, and cooled to −78° C. in a nitrogen atmosphere. 42 mL of a solution obtained by dissolving n-butyllithium in n-hexane at a concentration of 1.6 M was added thereto, and the mixture was stirred at −78° C. for 10 minutes for reaction. Thereafter, the mixture was heated to 0° C. and further stirred for 30 minutes. In this way, [1.1.1]propellane in a solvent (CPME/n-hexane) was obtained. A part of the obtained solution of [1.1.1]propellane was sampled, treated with water, and subjected to liquid separation. From $^1$H-NMR analysis of the organic phase, yield of [1.1.1]propellane was calculated. At this time, biphenyl was used as an internal standard. From the following data, it was confirmed that the [1.1.1]propellane was obtained.

Chemical shift σ (ppm) in $^1$H-NMR (400 MHZ, solvent: DMSO-d6, internal reference substance: tetramethylsilane (TMS))=2.04 (6H, s)

[Step (b)]

By using a yellow fluorescent lamp as a light source for illumination, environment was set in which light having a wavelength of 400 nm or less was completely shielded. A solution obtained by dissolving 9.0 g of iodine in 50 mL of CPME was added dropwise to the solution (0° C.) of [1.1.1]propellane obtained in the above-described step (a) over 5 minutes, and the mixture was stirred at 0° C. Thereafter, 30 mL of a 14% by mass sodium thiosulfate aqueous solution was added dropwise thereto over 3 minutes, the mixture was subjected to liquid separation, and the obtained organic phase was concentrated. The obtained concentrated organic phase was transferred to a flask, 10 mL of a 80% by volume methanol (MeOH) aqueous solution was added thereto, and the mixture was stirred at 5° C. and then filtered to obtain a crude product of 1,3-diiodo BCP. The obtained crude product was transferred to a flask, 7 mL of MeOH was added thereto, and the mixture was stirred at 5° C. and then filtered to obtain 1,3-diiodo BCP. From the following data, it was confirmed that the 1,3-diiodo BCP was obtained.

Chemical shift σ (ppm) in $^1$H-NMR (400 MHZ, solvent: DMSO-d6, internal reference substance: tetramethylsilane (TMS))=2.71 (6H, s)

Yields in each step of the step (a) and the step (b) are shown in the table below.

Examples 2 to 9

1,3-diiodo BCP was obtained in the same manner as in Example 1, except that, in Example 1, CPME used in the step (a) and the reaction temperature of −78° C. in the step (a) were changed as described in "Type of solvent in step (a)" and "Temperature in step (a)" in the table below, and the solvent of the iodine solution used in the step (b) was changed to the same solvent as "Type of solvent in step (a)" in the table below. In each of Examples, yields in each step of the step (a) and the step (b) are shown in the table below. In the table below, MTBE is methyl tert-butyl ether and $Bu_2O$ is dibutyl ether.

Comparative Examples 1 to 9

1,3-diiodo BCP was obtained in the same manner as in Example 1, except that, in Example 1, CPME used in the step (a) and the reaction temperature of −78° C. in the step (a) were changed as described in "Type of solvent in step (a)" and "Temperature in step (a)" in the table below, the solvent of the iodine solution used in the step (b) was changed to the same solvent as "Type of solvent in step (a)" in the table below, and the reaction in the step (b) was carried out in a state in which the light having a wavelength of 400 nm or less was not shielded (a white fluorescent lamp was used as the light source for illumination). In each of Comparative Examples, yields in each step of the step (a) and the step (b) are shown in the table below.

TABLE 1

| | Type of solvent in step (a) | Temperature in step (a) (° C.) | Yield in step (a) (%) | Yield in step (b) (%) |
|---|---|---|---|---|
| Example 1 | CPME | −78 | 70 | 95 |
| Example 2 | CPME | −50 | 68 | 95 |
| Example 3 | CPME | −40 | 60 | 95 |
| Example 4 | CPME | −30 | 52 | 97 |
| Example 5 | CPME | −20 | 43 | 97 |
| Example 6 | CPME | −10 | 35 | 95 |
| Example 7 | CPME | 0 | 17 | 97 |
| Example 8 | MTBE | −40 | 58 | 100 |
| Example 9 | $Bu_2O$ | −40 | 53 | 71 |
| Comparative Example 1 | CPME | −78 | 69 | 81 |
| Comparative Example 2 | CPME | −40 | 59 | 83 |
| Comparative Example 3 | CPME | 0 | 18 | 82 |
| Comparative Example 4 | MTBE | −78 | 69 | 85 |
| Comparative Example 5 | MTBE | −40 | 58 | 86 |
| Comparative Example 6 | MTBE | 0 | 22 | 84 |
| Comparative Example 7 | $Bu_2O$ | −78 | 65 | 56 |

TABLE 1-continued

| | Type of solvent in step (a) | Temperature in step (a) (° C.) | Yield in step (a) (%) | Yield in step (b) (%) |
|---|---|---|---|---|
| Comparative Example 8 | $Bu_2O$ | −40 | 53 | 58 |
| Comparative Example 9 | $Bu_2O$ | 0 | 23 | 57 |

As shown in the above table, in a case where the step (b) was performed by shielding the light having a wavelength of 400 nm or less, as compared with a case of not shielding the light, it was found that the yield in the step (b) was increased by 10% or more.

Even in a case where an acyclic ether solvent having 5 or 6 carbon atoms (MTBE or CPME) was not included as the type of the solvent in the step (b), the effect of the present invention (improvement of the yield of the step (b) by the light shielding) could be exhibited (comparison between Example 9 and Comparative Example 8). However, it was also found that the yield in the step (b) was lower as compared with a case where the acyclic ether solvent having 5 or 6 carbon atoms (comparison between Examples 3 and 8 and Example 9).

In addition, with regard to the step (a), it was found that, as the reaction temperature was lower, the yield tended to increase.

Example 10

1,3-diiodo BCP was obtained according to the following scheme.

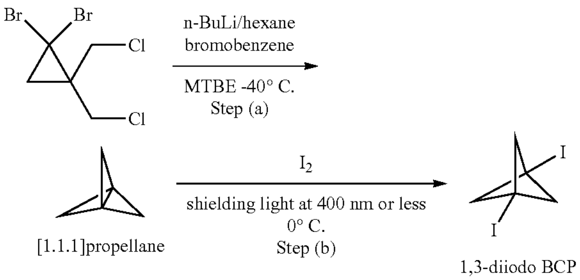

[1.1.1]propellane 1,3-diiodo BCP

[Step (a)]

40 mL of MTBE and 10.8 g of bromobenzene were charged into a 200 mL flask, and cooled to 0° C. in a nitrogen atmosphere. 43 mL of a solution obtained by dissolving n-butyllithium in n-hexane at a concentration of 1.6 M was added thereto, and the mixture was stirred for 1 hour. The obtained solution was added dropwise to a mixture of 60 mL of MTBE and 10 g of 1,1-dibromo-2,2-bis(chloromethyl) cyclopropane, which were charged into a 500 mL three-neck flask and cooled to −40° C. in a nitrogen atmosphere, over 40 minutes, and then the mixture was stirred at −40° C. for 10 minutes for reaction. Thereafter, the mixture was heated to 0° C. and further stirred for 30 minutes. In this way, [1.1.1]propellane in a solvent (MTBE/n-hexane) was obtained. The yield was calculated in the same manner as in Example 1.

[Step (b)]

By using a yellow fluorescent lamp as a light source for illumination, environment was set in which light having a wavelength of 400 nm or less was completely shielded. A solution obtained by dissolving 9.0 g of iodine in 50 mL of MTBE was added dropwise to the solution (0° C.) of [1.1.1]propellane obtained in the above-described step (a) over 5 minutes, and the mixture was stirred at 0° C. Thereafter, 30 mL of a 14% by mass sodium thiosulfate aqueous solution was added dropwise thereto over 3 minutes, the mixture was subjected to liquid separation, and the obtained organic phase was concentrated. The obtained concentrated organic phase was transferred to a flask, 10 mL of a 80% by volume MeOH aqueous solution was added thereto, and the mixture was stirred at 5° C. and then filtered to obtain a crude product of 1,3-diiodo BCP. The obtained crude product was transferred to a flask, 7 mL of MeOH was added thereto, and the mixture was stirred at 5° C. and then filtered to obtain 1,3-diiodo BCP. From $^1$H-NMR in the same manner as in Example 1, it was confirmed that the 1,3-diiodo BCP was obtained.

Yields in each step of the step (a) and the step (b) are shown in the table below.

Comparative Example 10

1,3-diiodo BCP was obtained in the same manner as in Example 10, except that, in Example 10, the reaction in the step (b) was carried out in a state in which the light having a wavelength of 400 nm or less was not shielded (a white fluorescent lamp was used as the light source for illumination). Yields in each step of the step (a) and the step (b) are shown in the table below.

TABLE 2

| | Yield in step (a) (%) | Yield in step (b) (%) |
|---|---|---|
| Example 10 | 70 | 97 |
| Comparative Example 10 | 68 | 83 |

In Example 10 and Comparative Example 10, bromobenzene and n-butyllithium were allowed to coexist in the step (a), and phenyllithium was produced in the reaction system. Even in this reaction system, it was found that the yield could be significantly increased by performing the step (b) by shielding the light of 400 nm or less, as specified in the present invention.

Example 11

1,3-diiodo BCP was obtained in the same manner as in Example 3, except that, in Example 3, an organic phase, which was obtained by obtaining the [1.1.1]propellane in the solvent in the step (a), the solution of [1.1.1]propellane was treated with water, and then subjecting the solution to liquid separation, was used as the solution (0° C.) of [1.1.1]propellane in the step (b). Yields in each step of the step (a) and the step (b) are shown in the table below.

Comparative Example 11

1,3-diiodo BCP was obtained in the same manner as in Example 11, except that, in Example 11, the reaction in the step (b) was carried out in a state in which the light having a wavelength of 400 nm or less was not shielded (a white fluorescent lamp was used as the light source for illumination). Yields in each step of the step (a) and the step (b) are shown in the table below.

TABLE 3

| | Yield in step (a) (%) | Yield in step (b) (%) |
|---|---|---|
| Example 11 | 55 | 97 |
| Comparative Example 11 | 55 | 82 |

In Example 11 and Comparative Example 11, the [1.1.1] propellane obtained in the step (a) was purified and used in the step (b). Even in this reaction system, it was found that the yield could be effectively increased by performing the step (b) by shielding the light of 400 nm or less, as specified in the present invention.

The present invention has been described with the embodiments thereof, any details of the description of the present invention are not limited unless described otherwise, and it is obvious that the present invention is widely construed without departing from the gist and scope of the present invention described in the accompanying claims.

What is claimed is:

1. A method for producing halogenobicyclo[1.1.1]pentane, comprising:

a step (a) of reacting 1,1-dibromo-2,2-bis(chloromethyl) cyclopropane with an organometallic reagent in a solvent including an acyclic ether solvent having 5 or more carbon atoms to obtain [1.1.1]propellane; and a step (b) of reacting the obtained [1.1.1]propellane with halogen in a solvent including an acyclic ether solvent having 5 or more carbon atoms in a state in which light having a wavelength of 400 nm or less is shielded to obtain halogenobicyclo[1.1.1]pentane.

2. The method for producing halogenobicyclo[1.1.1]pentane according to claim 1, wherein the organometallic reagent includes at least one of alkyllithium or aryllithium.

3. The method for producing halogenobicyclo[1.1.1]pentane according to claim 2, wherein the alkyllithium has 2 to 10 carbon atoms.

4. The method for producing halogenobicyclo[1.1.1]pentane according to claim 2, wherein the aryllithium is phenyllithium.

5. The method for producing halogenobicyclo[1.1.1]pentane according to claim 2, wherein the alkyllithium is butyllithium.

6. The method for producing halogenobicyclo[1.1.1]pentane according to claim 1, wherein a reaction temperature of the step (a) is set to 0° C. or lower.

7. The method for producing halogenobicyclo[1.1.1]pentane according to claim 1, wherein in the step (a) and the step (b), the acyclic ether solvent has 5 to 10 carbon atoms.

8. The method for producing halogenobicyclo[1.1.1]pentane according to claim 7, wherein in the step (a) and the step (b), the acyclic ether solvent has 5 or 6 carbon atoms.

9. The method for producing halogenobicyclo[1.1.1]pentane according to claim 1, wherein the halogen is iodine.

10. The method for producing halogenobicyclo[1.1.1] pentane according to claim 1, wherein the halogenobicyclo[1.1.1]pentane is diiodobicyclo[1.1.1]pentane.

11. The method for producing halogenobicyclo[1.1.1] pentane according to claim 1, wherein a step of distilling the [1.1.1]propellane is not provided.

* * * * *